United States Patent [19]

Sandborn

[11] Patent Number: 4,575,515

[45] Date of Patent: Mar. 11, 1986

[54] PHARMACEUTICAL SOLUTIONS COMPRISING DIMETHYL SULFOXIDE

[75] Inventor: Edmund Sandborn, Burlington, Canada

[73] Assignee: Clark Pharmaceutical Laboratories Ltd., Weston, Canada

[21] Appl. No.: 610,590

[22] Filed: May 15, 1984

[51] Int. Cl.$^4$ ............................................. A61K 31/10
[52] U.S. Cl. .................................. 514/708; 514/936; 514/647
[58] Field of Search ............................... 514/708, 936

[56] References Cited

U.S. PATENT DOCUMENTS

| | | | |
|---|---|---|---|
| 3,551,554 | 12/1970 | Herschler | 424/45 |
| 3,711,602 | 1/1973 | Herschler | 424/45 |
| 3,740,420 | 6/1973 | Herschler et al. | 424/45 |
| 3,743,727 | 7/1973 | Herschler | 514/936 |
| 4,353,896 | 10/1982 | Levy | 514/936 |
| 4,369,190 | 1/1983 | Schulte | 514/936 |

FOREIGN PATENT DOCUMENTS 1001075 12/1976 Canada.
1005761 2/1977 Canada.

*Primary Examiner*—Ronald W. Griffin
*Attorney, Agent, or Firm*—James D. Fornari; Ivor M. Hughes

[57] ABSTRACT

Novel pharmaceutical solutions and particularly novel pharmaceutical solutions comprising dimethyl sulfoxide (DMSO).

48 Claims, No Drawings

PHARMACEUTICAL SOLUTIONS COMPRISING DIMETHYL SULFOXIDE

FIELD OF INVENTION

This invention relates to novel pharmaceutical solutions and particularly novel pharmaceutical solutions comprising dimethyl sulfoxide (DMSO).

BACKGROUND OF THE INVENTION

If one rubs a few drops of DMSO on any part of his/her person, it is usually absorbed very rapidly an a taste resembling garlic is immediately present. This finding subsequently led to a most important finding of pharmacologic ability of pure DMSO of various strengths to reduce inflammation and pain in a wide range of conditions to penetrate into the skin after topical application of DMSO for the lessening of pain and swelling of inflammation. Many clinicians have reported particularly gratifying results by the use of DMSO in the management of arthritis.

U.S. Pat. No. 3,549,770 teaches the topical application of undiluted dimethyl sulfoxide, and dimethyl sulfoxide with appropriate pharmaceutical diluents, excipients and adjuvants in the treatment of tissue damage, pain, abnormal muscle contraction and vascular insufficiency.

The facility with which DMSO penetrates the skin and other membranes has spawned considerable research into the use of DMSO as a vehicle for the administration of drugs through topical application. In the course of that research a number of different products were added to DMSO with ranging degrees of success.

U.S. Pat. No. 3,711,606 teaches the use of DMSO as a carrier in concentrations of 50% and over by weight with a steroid in lotion, cream, gel and ointment forms to penetrate rapidly to and saturate the stratum corneum, the highly resistant "horny layer" of the skin which is the major barrier to penetration.

According to this patent "The Steroid continues to penetrate through the skin from 'this reservoir' in the stratum corneum to the underlying tissue and into the circulatory system" (Column 3, Line 50-53).

U.S. Pat. No. 3,711,602 also teaches the compositions (creams, suppositories, ointments and gels) for topical application for enhancing tissue penetration of physiologically active agents (for example, physiologically active steroids, antineoplastic agents, antigens, antihistamine agents, neuropharmacologic agents, anti-inflammatory agents, anticoagulants, vasodilators, ultra-violet screening agents and agents with DMSO.

However, these compositions are extremely greasy and are soley for surface penetration, very little penetrating deeply into affected areas where the greatest need arises. See also U.S. Pat. Nos. 3,551,554; 3,740,420; 3,743,727; 3,790,682; 4,369,190 and 3,499,961 and Canadian Letters Patent Nos. 1,001,075; 1,011,255; 1,043,704; 980,252 and 1,005,761.

Furthermore these compositions are not suitable where there is a need for rapid deep penetration of medicine for direct application to an affected part of the body (joints etc.). In addition, DMSO also captures water from the skin, being a hydroxyl ion scavenger thereby dehydrating the skin.

It is therefore, an object of this invention to provide penetrating solutions, allowing penetration deeply into affected parts of the body, comprising DMSO, preferably another medicine which may be applied topically and which rapidly penetrates deeply into the body carrying the medication in the solutions with it while protecting the skin against dehydration.

Further and other objects of the invention will be realized by those skilled in the art from the following summary of the invention and detailed description of the embodiments thereof.

SUMMARY OF THE INVENTION

According to one aspect of the invention, a deeply and rapidly penetrating homogeneous solution for topical application causing medicine to penetrate deeply and rapidly into affected parts of the body without irritating the skin or leaving a greasy film on the skin when the solution is applied topically is provided, the solution comprising:

(a) between about 40% and about 85% DMSO by weight of the solution, more preferably between about 60% and about 70% DMSO by weight of the solution of most preferably about 65% DMSO by weight of the solution;

(b) a polyalcohol, preferably having 3-5 carbon atoms, for the retention of moisture in the skin, in one embodiment, glycerol or glycerine;

(c) a dispersant for assisting to disperse the components in solution to provide a homogeneous solution when applied to the skin and when penetrating the skin, in one embodiment propylene glycol;

(d) a medicine, for example Naproxen and Diclofenac dissolved in the solution;

(e) water.

Because the medicine must be dissolved in the solution, a solubilizing agent may be added to the solution to dissolve the medicament. For example, Naproxen is not soluble in DMSO. Therefore, Ethanol is used to solubilize the Naproxen for addition to the solution. Xylocaine may also be added to the solution where desired.

When the penetrating solutions of the invention are employed in topical applications unexpected results from treatment therewith are obtained. This is because of the ability of the solution to penetrate quickly and deeply into the body through the skin and tissue below the point of topical application. Furthermore, because of the nature of the solution, the skin is not dried out. Where glycerol is employed, glycerol is a hydroxyl radical scavenger (as is DMSO) and assists in the medicinal effect of the DMSO in the solution. The dispersant propylene glycol is also a hydroxyl radical scavenger.

The formulations are prepared by combining the requisite amounts of the ingredients together (adding solubilizing agents, for example Ethanol where Naproxen is to be included). The medicines that may be used with the DMSO may be manufactured according to the processes taught in the following patents or other such suitable processes.

| | |
|---|---|
| NAPROXEN: | Canadian Letters Patent: 1,122,603 1,004,226 1,142,957 1,137,108 879,118 879,719 936,171 955,600 960,668 960,689 983,517 991,655 1,000,725 1,000,726 1,020,575 1,124,735 |
| DICLOFENAC: | Canadian Letters Patent: 850,133 811,738 829,910 918,175 765,432 827,708 1,126,746 1,050,565 |
| NIFEDIPINE: | Canadian Letters Patent: 981,582 934,758 868,911 921,035 1,080,223 |

The invention will now be illustrated having regard to the following embodiments and exemplary test cases.

EMBODIMENTS

DMSO with Diclofenac as a treatment for arthritis.

| | |
|---|---|
| 300 ml | 90% DMSO |
| 60 ml | glycerine |
| 25 ml | propylene glycol |
| 100 ml | water |
| 15 ml | ethyl alcohol |
| 75 gm | Diclofenac |

Solution as a treatment for Psoriasis

| | |
|---|---|
| 65 ml | 90% DMSO |
| 3.375 gm | Diclofenac |
| 80 ml | $H_2O$ |
| 5 ml | 2% Xylocaine |
| 250 ml | ethyl alcohol |
| 65 ml | glycerine |
| 30 ml | propylene glycol |
| 5 ml | tar |

DMSO with Diclofenac & Urea as a treatment for Arthritis with added skin protection.

| | |
|---|---|
| 325 ml | DMSO 90% |
| 70 ml | $H_2O$ |
| 50 gm | Urea |
| 25 ml | Glycerine |
| 75 gm | Diclofenac |
| 25 ml | Propylene Glycol |

Solution for treatment of Herpes

| | |
|---|---|
| 335 ml | DMSO 90% |
| 25 ml | Glycerol |
| 25 ml | Propylene glycol |
| 100 ml | $H_2O$ |
| 15 ml | Ethyl Alcohol |
| 75 gm | Diclofenac |

The following case histories are offered where penetrating solutions according to the invention are employed.

In each of the cases set out below, the anti-inflammatories used were Naproxen or Diclofenac.

CASE 1

Mrs. E. G.-Age 58 Years-Rheumatoid Arthritis

Severe pain in left tarsal joint, then late in May, right foot then rapidly involved right leg, both shoulders, elbows, and wrists. Was first treated with phenylbutazone, then Naproxen, but four months later was becoming severly disabled with acute symptoms particularly shoulders, wrists and right foot-33 joints involved. Thereafter, treatment with penetrating solution comprising DMSO with Naproxen, Ethanol, water, propylene glycol and glycerine by the topical application thereof. Indocid was administered by mouth. By the next month some improvement in mobility, but shoulders still only slight (10) abduction. Treatment was continued five times daily. Three months later remarkable improvement in mobility. Three months later, returned to work part-time.

This patient has shown steady improvement with essentially full return to range of motion in all joints. Still employs DMSO by itself for flare-ups, can go without medication.

CASE 2

Mrs. B., W.-Age 52 Years-Post Traumatic Arthritis

Ankle-skiing accident with comminuted fracture-repaired by surgical intervention with numerous screws and plates-one screw later removed. After 13 years of restricted movement and acute pain, patient was advised that if she was not prepared to tolerate the pain—the only alternatives were fusion or amputation. Began trial with topical application of a penetrating solution of DMSO anti-inflammatories, propylene, glycol, water and glycerine. Within days mobility began to improve and this was gradually followed by a reduction in pain. Four months later, almost complete return of function and was pain free. Now only employs DMSO at irregular intervals.

CASE 3

Mrs. J. F.-Age 52 years-Traumatic Arthritis

Fractured left ankle on three occasions-each repaired by open reduction. Movements severely restricted and pain severe, employed crutches-has done so for three years. Began topical treatment with formulation used in Case 1. After treatment, flexibility and comfort both improving—can bear some weight. A month later, flexibility improving but still a long way to go. However, lateral and medial movement of tarsal joints had improved considerably but dorsiflection still quite limited. Four months later can finally touch heel to floor. Some months later, ankle greatly improved both mobility improved and pain quite tolerable—has been able to live normally, walks, dances, etc. has had bouts of gouty arthritis in other foot but this is also under satisfactory control.

CASE 4

Mr. H. B.-Age 63 Years-Arthritis

Arthritis in wrists, hands, ankle, feet and back.

Arthritis recurrent exacerbations for 22 years. Has reached the point where wrists and ankles are almost completely ankylosed-very little movement obtainable is not able to continue at work. Barely able to walk—began topical application of penetrating solution comprising DMSO anti-inflammatory, propylene glycol, glycerine, water. Improvement was seen quite rapdily by reduction of effusion and slow increase of mobility over the years, in spite of exacerbations of acute arthritis, his mobility has increaded until he can walk much better,-lifestyle closer to normal.

CASE 5

Mr. M. L.-Age 51 Years-Osteoarthritis

Right knee, began following a football injury 30 years ago-had meniscus excised. Activities quite limited due to pain. Began topical application of penetrating solution comprising DMSO, anti-inflammatory, propylene glycol, glycerine and water. Exercise tolerance and comfort improved steadily. Patient has been able to participate in sports in more comfort.

CASE 6

Mr. K. L.-Age 62 Years-Osteoarthritis

Knees, has had one cartlidge removed-unable to participate in sports without pain. Begam topical application of formulation used in Case 1. Increased ability to participate in sports. Improvement still maintained in spite of acute flare-ups on occasion.

CASE 7

Mr. B. P.-Age 59 years-Acute Bursitis and Arthritis

Acute Bursities left shoulder. Abduction only 150. Acute pain in both knees from degenerated cartilages and osteoarthritis. Patient began topical treatment with penetrating solution comprising DMSO, anti-inflammatory, propylene glycol, glycerine and water after arthroscopy and by the time his surgical booking had arrived, he was so much improved he refused the surgical procedure. His pain gradually receded, mobility of knees and shoulder increased until he was able to live in comfort and return to active work and sports without pain. He now only requires occasional application of DMSO solution for slight discomfort.

CASE 8

Age 64 years

Patient diagnosed as having neuromuscular rheumatism and advised prolonged bed rest-suggested period three years. Patient has marked crepitus joints-had been told "her chances of working again were non-existent" (Mayo Clinic). Patient was a practical nurse who had re-entered a registered nursing training course but was forced to stop due to illness-when first seen was in a wheel chair and even had great difficulty in swallowing. After treatment with penetrating solution comprising DMSO, anti-inflammatory, propylene, glycol glycerine and water for several days, a slight increase in movement of joints was detectable. A month later, feels immensely better and flexion and rotation of shoulders has increased dramatically. She has an excellent response. Subsequently returned to nursing school, works three nights a week and has returned to driving an automobile. This patient has obtained full function of joints and muscles; has completed her nursing training and has worked full time since. She has now entered the B.Sc. nursing training course and is doing very well.

As many changes can be made to the embodiments disclosed without departing from the scope of the invention, it is intended that all material contained herein be interpreted as illustrative of the invention and not in a limiting sense.

We claim:

1. A deep and rapidly penetrating homogeneous solution for topical application causing medicine to penetrate deeply into affected parts of the body without irritating the skin or leaving a greasy film on the skin when the solution is applied topically, the solution comprising:
   (a) between about 40% and about 85% DMSO by weight of the solution;
   (b) a polyalcohol for assisting to retain moisture in the skin and prevent the skin from dehydrating;
   (c) dispersant for assisting to disperse the components in solution to provide a homogeneous solution when applied and when penetrating the skin
   (d) a medicine
   (e) water.

2. The solution of claim 1, wherein the medicine is Naproxen, ethanol is added as a solubilizing agent.

3. The solution of claim 1, wherein the medicine is Nifedipine.

4. The solution of claim 1, wherein the medicine is Diclofenac.

5. The solution of claim 1, wherein the polyalcohol has 3-5 carbon atoms.

6. The solution of claim 2, wherein the polyalcohol has 3-5 carbon atoms.

7. The solution of claim 3, wherein the polyalcohol has 3-5 carbon atoms.

8. The solution of claim 4, wherein the polyalcohol has 3-5 carbon atoms.

9. The solution of claim 1, wherein the polyalcohol is glycerol (glycerine).

10. The solution of claim 2, wherein the polyalcohol is glycerol (glycerine).

11. The solution of claim 3, wherein the polyalcohol is glycerol (glycerine).

12. The solution of claim 4, wherein the polyalcohol is glycerol (glycerine).

13. The solution of claim 1, wherein the DMSO is present between about 60% and about 70% by weight of the solution.

14. The solution of claim 1, wherein the DMSO constitutes about 65% by weight of the solution.

15. The solution of claim 1, wherein the dispersant is propylene glycol.

16. The solution of claim 2, wherein the DMSO is present between about 60% and about 70% by weight of the solution.

17. The solution of claim 2, wherein the DMSO constitutes about 65% by weight of the solution.

18. The solution of claim 2, wherein the dispersant is propylene glycol.

19. The solution of claim 3, wherein the DMSO is present between about 60% and about 70% by weight of the solution.

20. The solution of claim 3, wherein the DMSO constitutes about 65% by weight of the solution.

21. The solution of claim 3, wherein the dispersant is propylene glycol.

22. The solution of claim 4, wherein the DMSO is present between about 60% and about 70% by weight of the solution.

23. The solution of claim 4, wherein the DMSO constitutes about 65% by weight of the solution.

24. The solution of claim 4, wherein the dispersant is propylene glycol.

25. The solution of claim 5, wherein the DMSO is present between about 60% and about 70% by weight of the solution.

26. The solution of claim 5, wherein the DMSO constitutes about 65% by weight of the solution.

27. The solution of claim 5, wherein the dispersant is propylene glycol.

28. The solution of claim 6, wherein the DMSO is present between about 60% and about 70% by weight of the solution.

29. The solution of claim 6, wherein the DMSO constitutes about 65% by weight of the solution.

30. The solution of claim 6, wherein the dispersant is propylene glycol.

31. The solution of claim 7, wherein the DMSO is present between about 60% and about 70% by weight of the solution.

32. The solution of claim 7, wherein the DMSO constitutes about 65% by weight of the solution.

33. The solution of claim 7, wherein the dispersant is propylene glycol.

34. The solution of claim 8, wherein the DMSO is present between about 60% and about 70% by weight of the solution.

35. The solution of claim 8, wherein the DMSO constitutes about 65% by weight of the solution.

36. The solution of claim 8, wherein the dispersant is propylene glycol.

37. The solution of claim 9, wherein the DMSO is present between about 60% and about 70% by weight of the solution.

38. The solution of claim 9, wherein the DMSO constitutes about 65% by weight of the solution.

39. The solution of claim 9, wherein the dispersant is propylene glycol.

40. The solution of claim 10, wherein the DMSO is present between about 60% and about 70% by weight of the solution.

41. The solution of claim 10, wherein the DMSO constitutes about 65% by weight of the solution.

42. The solution of claim 10, wherein the dispersant is propylene glycol.

43. The solution of claim 11, wherein the DMSO is present between about 60% and about 70% by weight of the solution.

44. The solution of claim 11, wherein the DMSO constitutes about 65% by weight of the solution.

45. The solution of claim 11, wherein the dispersant is propylene glycol.

46. The solution of claim 12, wherein the DMSO is present between about 60% and about 70% by weight of the solution.

47. The solution of claim 13, wherein the DMSO constitutes about 65% by weight of the solution.

48. The solution of claim 12, wherein the dispersant is propylene glycol.

* * * * *